(12) United States Patent
Woltermann et al.

(10) Patent No.: US 7,638,635 B2
(45) Date of Patent: Dec. 29, 2009

(54) USING ALKYLMETAL REAGENTS FOR DIRECTED METALATION OF AZAAROMATICS

(75) Inventors: Christopher J. Woltermann, Gastonia, NC (US); Douglas E. Sutton, Kings Mountain, NC (US)

(73) Assignee: FMC Corporation Lithium Division, Philadelphia, PA (US)

( * ) Notice: Subject to any disclaimer, the term of this patent is extended or adjusted under 35 U.S.C. 154(b) by 264 days.

(21) Appl. No.: 11/539,940

(22) Filed: Oct. 10, 2006

(65) Prior Publication Data

US 2007/0249838 A1 Oct. 25, 2007

Related U.S. Application Data

(63) Continuation of application No. 10/818,588, filed on Apr. 6, 2004, now Pat. No. 7,129,360.

(60) Provisional application No. 60/460,994, filed on Apr. 7, 2003.

(51) Int. Cl.
C07D 213/63 (2006.01)
(52) U.S. Cl. ...................... 546/290; 546/298
(58) Field of Classification Search .................. 546/290, 546/298
See application file for complete search history.

(56) References Cited

U.S. PATENT DOCUMENTS

| | | | |
|---|---|---|---|
| 3,197,516 A | 7/1965 | Esmay et al. | |
| 3,429,829 A | 2/1969 | Kahle | |
| 3,446,860 A | 5/1969 | Beumel, Jr. | |
| 3,511,884 A | 5/1970 | Smith, Jr. | |
| 3,534,113 A | 10/1970 | Eastham et al. | |
| 4,006,187 A | 2/1977 | Kamienski et al. | |
| 5,262,556 A | 11/1993 | Riefling et al. | |
| 5,530,145 A * | 6/1996 | Wang et al. | 549/328 |
| 5,626,798 A | 5/1997 | Schwindeman et al. | |
| 5,670,691 A | 9/1997 | Spangler et al. | |
| 5,976,403 A | 11/1999 | Dover et al. | |
| 6,054,583 A | 4/2000 | Kelly et al. | |
| 6,657,093 B2 | 12/2003 | Meudt et al. | |
| 2004/0073032 A1 | 4/2004 | Meudt et al. | |

FOREIGN PATENT DOCUMENTS

WO WO 92/19622 A1 11/1992

OTHER PUBLICATIONS

Comins et al., "Lithiation of Methoxypyridines Directed by ∝-Amino Alkoxides", J. Org. Chem. 55:69-73 (1990).
International Search Report corresponding to PCT/US04/11661, mailed Feb. 14, 2005.
A. Guijarro et al., "Naphthalene-catalysed lithiation of functionalized chloroarenes: regioselective preparation and reactivity of functionalized lithioarenes", Tetrahedron 49:469-482 (1993), Abstract.
D. Guijarro et al., "Arene-Catalysed Lithiation of Fluoroarenes", Tetrahedron 56:1135-1138 (2000), Abstract.
M. Schlosser "Organometallics in Synthesis", *Wiley* pp. 289-293 (2002).
Marsais et al. "Regioselective alpha-lithiation of 3-alkoxypyridines: a ortho-disubstituted pyridines", *Synthesis* pp. 235-237 (1982).
Winkle et al. "Regioselective metalation reactions of some substituted (methoxymethoxy) arenes", *J. Org. Chem.* 47:2101-2108 (1982).
Maih et al. "Directed ortho metalation of pyridyl carbamates. Regiospecific entries into polysubstituted pyridines", *J. Org. Chem.* 50:5436-5438 (1985).
Comins et al. "Ortho lithiation of 2-, 3-, and 4-methoxypyridines", *Tetrahedron Letters* 29(7):773-776 (1988).
Supplementary European Search Report corresponding to European application No. 04750181.2 dated Mar. 19, 2009.

* cited by examiner

*Primary Examiner*—Rei-tsang Shiao
(74) *Attorney, Agent, or Firm*—Myers Bigel Sibley & Sajovec, PA

(57) ABSTRACT

Substituted alkylmetal reagents such as (trimethylsilylmethyl)lithium are reacted with pyridinic compounds to produce functionalized pyridinic compounds.

7 Claims, 1 Drawing Sheet

USING ALKYLMETAL REAGENTS FOR DIRECTED METALATION OF AZAAROMATICS

CROSS-REFERENCE TO RELATED APPLICATIONS

Figure 1:
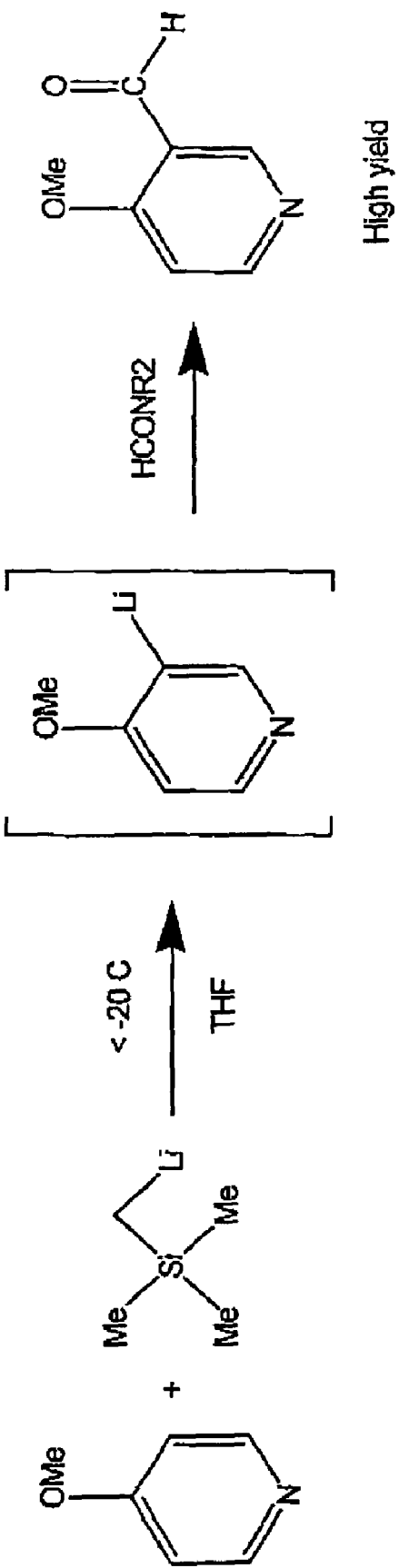

The present continuation application claims priority to U.S. patent application Ser. No. 10/818,588, filed on Apr. 6, 2004 now U.S. Pat. No. 7,129,360 which claims priority to U.S. Provisional Application No. 60/460,994, filed Apr. 7, 2003, the disclosures of which are incorporated herein by reference in their entireties.

FIELD OF THE INVENTION

This invention relates to the metalation of chemical compounds and more generally to the metalation of azaaromatics and to compositions used in the metalation of chemical compounds.

BACKGROUND OF THE INVENTION

Functionalized azaaromatic compounds, such as pyridines, quinolines, and pyrimidines, may be used as substructures in biologically active compounds. For instance, functionalized azaaromatic compounds are useful in the pharmaceutical industry, such as in the treatment of central nervous system disorders.

Traditional methods and procedures for creating functionalized azaaromatic compounds employ metalation techniques. Azaaromatics may be metallated by the deprotonation of the azaaromatic compound using bases such as lithium amides. Although lithium amides, such as lithium diisopropylamide (LDA) and lithium tetramethylpiperidide, have been used to deprotonate azaaromatic compounds, lithium amides are often not a strong enough base to completely deprotonate the azaaromatic compound. Furthermore, yields of functionalized azaaromatics produced by deprotonation with lithium amides tend to be modest. The use of other alkyllithium reagents, such as n-butyllithium, has also been undesirable because alkyllithiums, such as n-BuLi or tert-BuLi, tend to nucleophilicly attack the imine functionality of the azaaromatic compounds. In some cases, alkyllithiums with a catalytic amount of a secondary amine present can effectively deprotonate azaaromatics. This "catalyzed metalation" technique often produces modest yields. The modest yields may result because there is competing addition of the alkyllithium to the carbon-nitrogen double bond. As an alternative, the use of stronger bases has been proposed and tested for functionalization reactions of azaaromatic compounds. For instance, strong bases and poor nucleophiles such as lithium 2,2,6,6-tetramethylpiperidine (LiTMP) and mesityllithium (MesLi) have been used to functionalize azaaromatic compounds. However, the use of LiTMP and MesLi in industrial practice to produce large quantities of functionalized azaaromatic compounds is limited because the reactants are not readily available, they often require very low temperatures and/or the formation processes cannot be easily adapted to large-scale commercial production processes.

Methods for facilitating the metalation of azaaromatic compounds, which are scalable and produce high yields, are therefore desirable. Furthermore, methods, processes, and compounds for facilitating the metalation of azaaromatic compounds and other chemical compounds are also desirable.

SUMMARY OF THE INVENTION

Embodiments of the present invention generally relate to the deprotonation of azaaromatic compounds such as nitrogen containing six-membered rings, pyridines, quinolines, pyrimidines, pyridazines, pyrazines, pteridines, phthalazines, triazines, tetrazines, and the like. According to some embodiments, direct deprotonation of an azaaromatic compound may be accomplished by reacting an azaaromatic compound with a substituted alkylmetal reagent. The reaction may occur with or without added catalyst. In various embodiments, the substituted alkylmetal reagent, for example (trimethylsilylmethyl)lithium (TMSMLi) is reacted in stoichiometric amounts with an azaaromatic compound to produce a lithiated azaaromatic compound that can be reacted with an electrophile to produce a functionalized azaaromatic compound.

In other embodiments of the present invention, the solubility and storage stability of a substituted alkylmetal reagent are improved by including an ether in the storage mixture. According to some embodiments, methyl tert-butyl ether (MTBE) may be added to a (trimethylsilylmethyl)lithium composition to improve the stability of the (trimethylsilylmethyl)lithium composition.

The use of substituted alkylmetal reagents to deprotonate azaaromatics produces improved yields and provides scalability to the direct deprotonation process, which have not been realized in other deprotonation processes.

BRIEF DESCRIPTION OF THE DRAWING FIGURES

The invention can be more readily ascertained from the following description of the invention when read in conjunction with the accompanying drawings in which:

FIG. 1 illustrates a reaction scheme according to an embodiment of the invention.

DETAILED DESCRIPTION OF THE INVENTION

The present invention now will be described more fully hereinafter with reference to the accompanying drawing, in which some embodiments of the invention are shown. This invention may, however, be embodied in many different forms and should not be construed as limited to the embodiments set forth herein.

According to embodiments of the present invention, compounds and/or reagents for facilitating deprotonation of azaaromatic compounds are provided. In some embodiments, an alkylmetal reagent is provided to facilitate the direct deprotonation of an azaaromatic compound. In other embodiments of the invention, alkylmetal reagents may be used to facilitate the deprotonation of chemical compounds other than azaaromatics.

In various embodiments of the invention, a substituted alkylmetal reagent may be used for the direct deprotonation of an azaaromatic compound. The use of a substituted alkylmetal reagent as a deprotonation agent minimizes the nucleophilic attack on the imine functionality of the azaaromatic compound. The direct deprotonation and minimized nucleophilic attack on an azaaromatic compound results in improved yields and simplified purification schemes for the deprotonation reactions.

Examples of azaaromatic compounds that may be deprotonated by the substituted alkylmetal reagents according to embodiments of the present invention include nitrogen containing six-member ring systems, such as pyridines, quinolines, isoquinolines, acridines, phenanthridines, quinoxalines, oxazines, thiazines, purines, pyrimidines, pyridazines, pyrazines, pteridines, phthalazines, triazines, tetrazines, and the like. For example, 4-methoxypyridine, 2-fluoropyridine, 2-methoxypyridine, and 3-methoxypyridine may be deprotonated according to embodiments of the present invention. Other azaaromatic compounds may also be deprotonated by substituted alkylmetal reagents according to embodiments of the present invention.

Alkylmetal reagents used with embodiments of the present invention may include hindered methylmetal reagents and/or substituted methylmetal reagents. For example, according to various embodiments of the invention, (trimethylsilylmethyl) lithium is used as a substituted alkylmetal reagent and is reacted with an azaaromatic compound. The use of (trimethylsilylmethyl)lithium to directly deprotonate an azaaromatic compound minimizes the nucleophilic attack on the imine functionality of the azaaromatic compound. Furthermore, only a stoichiometric amount of the (trimethylsilylmethyl) lithium is required in the reaction, resulting in improved yields and simple purification schemes.

Substituted alkylmetal reagents used with embodiments of the present invention preferably exhibit excellent stability. Some substituted methylmetal reagents, such as (trimethylsilylmethyl)lithium, exhibit excellent stability because there is no possibility of 1,2-elimination of the metal hydride in the composition. The reduced elimination of metal hydride in the composition allows the composition to be prepared, isolated, and stored for extended periods of time.

A reaction scheme according to embodiments of the present invention is illustrated in FIG. 1. As illustrated in FIG. 1, methoxypyridine is deprotonated using the alkylmetal reagent (trimethylsilylmethyl)lithium. According to embodiments of the present invention, 4-methoxypyridine may be reacted with (trimethylsilylmethyl)lithium then N-formylpiperidine to produce 4-methoxy-3-pyridinecarboxaldehyde (MPC). The reaction is carried out at a temperature of about −20° C. or less in the presence of tetrahydrofuran (THF). $HCONR_2$ is also added to the reaction mixture, wherein R is an alkyl group, for example, dimethylformamide or 1-formylpiperidine. The resulting 4-methoxy-3-pyridinecarboxaldehyde is crystallized directly from the reaction mixture with yields between about 60 percent to about 100 percent MPC, depending on temperature used. For example, in the reaction scheme of FIG. 1, a 60 percent yield was achieved at −10° C. and a 100 percent yield was achieved at −30° C. Yields may be higher at temperatures below about −20° C. but are still acceptable at higher temperatures, for example at about −12° C. or higher. The presence of directed ortho metallating groups gives typical selectivity for deprotonation on the aromatic rings. Likewise, lateral lithiation, where side chains on the aromatic ring are metallated, is possible with these bases.

Other embodiments of the invention include the use of other substituted alkylmetal reagents and methyllithiums, such as neopentyllithium, for functionalizing pyridines and nitrogen heterocycles. The use of (trimethylsilylmethyl) lithium, however, may be preferred to neopentyllithium because it has much higher solubility in hydrocarbon solvents (14% vs 5%). Other beta-substituted alkylmetals, alkyllithium and/or substituted methylmetal reagents may also be used with embodiments of the invention. For example, bis-(trimethylsilyl)methyllithium, tris-(trimethylsilyl)methyllithium and isobutyllithium may be used for functionalizing azaaromatics. Embodiments of the invention also include the use of compounds having the general formula $R_3W—CH_2—M$ for the deprotonation of azaaromatics, wherein R is an alkyl, aryl, or Si; W is carbon, Si, or Sn; and M is one or more metals selected from the group consisting of lithium, sodium, potassium, cesium, manganese, zinc, and magnesium.

No nucleophilic attack of the azaaromatic compounds used with the alkylmetal reagents of the invention has been detected. Further, only a stoichiometric amount of the alkylmetal reagents are required. The methods and processes of the embodiments of the invention have provided excellent yields of desired product. In addition, the processes and methods are easily scalable, providing commercial viability to the embodiments of the present invention.

Other embodiments of the present invention involve the formation of substituted alkylmetal reagent compositions and particularly the formation of storage-stable substituted alkylmetal reagent compositions. For instance, according to some embodiments of the present invention, (trimethylsilylmethyl) lithium may be mixed with a molar equivalent of methyl tert-butyl ether (MTBE) to enhance the solubility of the (trimethylsilylmethyl)lithium and improve the storage and handling stability of the composition.

Typically, substituted alkylmetal reagents such as (trimethylsilylmethyl)-lithium are mixed with hexanes for storage and handling. The addition of hexanes to (trimethylsilylmethyl)lithium compositions provides stability to the (trimethylsilylmethyl)lithium composition up to about 8 weight percent of (trimethylsilylmethyl)lithium in the composition at about 5° C. Mixtures of (trimethylsilylmethyl)lithium in hexanes exceeding about 8 weight percent (trimethylsilylmethyl) lithium at 5° C. are pyrophoric, tending to spontaneously ignite. Thus, trimethylsilymethyllithium compositions mixed with hexanes must not exceed about 8 percent by weight if they are being used at or below 5° C.

According to other embodiments of the present invention, an alkylmethyl reagent mixture may be stabilized for storage and handling by the addition of an ether to the alkylmethyl reagent mixture. For example, substituted alkylmetal reagents, such as (trimethylsilylmethyl)lithium, are stabilized for storage and handling by the addition of an ether in an amount of about 0.5 molar equivalents to about 3 molar equivalents, or between about 0.5 molar equivalent to about 1.5 molar equivalents, to the substituted alkylmetal reagent. Ethers that may be used with embodiments of the present invention include, but are not limited to, methyl tert-butyl ether, diethyl ether, dimethyl ether, dibutyl ether, cyclopentyl methyl ether, diisopropyl ether, dipropyl ether, dimethoxymethane, dimethoxyethane, diethoxyethane, dioxane, diglyme, triglyme, tetraglyme and methyl tetrahydrofurans.

According to embodiments of the present invention, methyl tert-butyl ether is added to a (trimethylsilylmethyl) lithium composition to improve the stability of the composition. The addition of one or more molar equivalents of methyl tert-butyl ether to a (trimethylsilylmethyl)lithium composition allows an increased amount of (trimethylsilylmethyl) lithium to be added to the composition mixture. For example, mixtures of hexanes and (trimethylsilylmethyl)lithium having about 25 percent by weight (trimethylsilylmethyl)lithium may be produced, used, and stored at or below about 5° C. with the addition of methyl tert-butyl ether to the mixture. The addition of methyl tert-butyl ether also enhances the solubility of the mixture.

According to embodiments of the present invention, methyl tert-butyl ether is added to a (trimethylsilylmethyl) lithium composition or (trimethylsilylmethyl)lithium and hexane mixture. The methyl tert-butyl ether is preferably added to the (trimethylsilylmethyl)-lithium mixture following the formation of the (trimethylsilylmethyl)lithium and is preferably added in a one mole equivalent. However, in other embodiments of the present invention the methyl tert-butyl ether is added in an amount between about 0.5 molar equivalents of (trimethylsilylmethyl)lithium and about 3 molar equivalents of (trimethylsilylmethyl)lithium.

The various embodiments of the present invention may be used in the production of agents or chemical compounds for use in the production of pharmaceuticals, for instance, the production of MPC. Functionalized azaaromatic compounds are often used as substructures in biologically active compounds. For example, pyridine-based pharmaceutical intermediates, such as halo- and methoxypyridines, may be formed by directed ortho lithiation of functionalized pyridines. The use of pyridine-based intermediates in the pharmaceutical industry is limited, however, by production levels. Heretofore, production levels of some pyridine-based pharmaceuticals were limited to bench scale quantities having poor yields. The poor yields and difficulty in scaling the reactions to commercial production levels has made the cost of such compounds high. Using the various embodiments of the invention, yield quantity may be increased and production levels may be improved because the processes and methods of the embodiments of the invention are easily scalable.

The improved yield quantities and increased production can be illustrated by a number of examples. For instance, the formation of 4-methoxy-3-pyridinecarboxaldehyde using embodiments of the present invention produces better yields at higher temperatures. The formation of 2-methoxy-3-pyridineboronic acid using LDA and traditional methods for functionalizing azaaromatic compounds produces a 13 percent yield, whereas embodiments of the present invention produce about 68 percent yields for such reaction. In addition, the formation of 2-fluoro-3-pyridinecarboxaldehyde has been reported at a 60 percent yield using PhLi and LDA, whereas embodiments of the present invention achieve about 90 percent yields.

EXAMPLES

Examples, although not optimized, illustrating particular embodiments of the invention follow:

Example 1

Deprotonation of Azaaromatic Using (trimethylsilylmethyl)lithium

A solution of (trimethylsilylmethyl)lithium (106 mL, 12.8 weight percent in hexanes) was charged to a 250 mL 3-neck round-bottom flask and cooled to −40° C. A solution of 4-methoxypyridine (10.0 g) in tetrahydrofuran (THF) (111 mL) was added at less than −30° C. over one hour. The lithiation was complete after about 1.5 hours. 1-Formylpiperidine (10.6 g) was added at −35° C. over 5 minutes. After 1.5 hours the reaction mixture was quenched with acetic acid (15 mL) and water (35 mL). The aqueous layer was separated and washed with 4×25 mL EtOAc. All organic layers were combined, dried over MgSO₄ and concentrated in vacuo to leave 16.0 g of yellow oil that crystallized on cooling. After trituration with 30 mL hexanes/1 mL isopropyl alcohol, this material was 96.5% pure by GCarea % (13.02 g, 99% yield, corrected for assay). Recrystallization from IPA/hexanes (1:3) gave an 83% yield of desired product as pale yellow crystals.

Example 2

Deprotonation of Azaaromatic Using (trimethylsilylmethyl)lithium

A solution of (trimethylsilylmethyl)lithium (22 mL, 13.8 weight percent in hexanes) was charged to a 100 mL 3-neck round-bottom flask and cooled to −50° C. A solution of 2-fluoropyridine (2.0 g), THF (25 mL) and diisopropylamine (0.13 mL) was added at less than −50° C. in 1 minute. After 3 hours, 1-formylpiperidine (2.4 g) was added in 1 min at less than −50° C. The mixture was allowed to warm to room temperature and stir overnight. The reaction mixture was quenched with acetic acid (3 mL) and water (7 mL). The aqueous layer was separated and washed with 3×25 mL MTBE. All organic layers were combined, dried over MgSO₄ and concentrated in vacuo to leave 3.79 g of brown oil. This oil was chromatographed through silica gel, eluting with 15% EtOAc in hexanes, to afford 2.24 g of 92.4% pure 2-fluoro-3-pyridinecarboxaldehyde (90% yield, corrected for assay).

Example 3

Deprotonation of Aazaaromatic Using (trimethylsilylmethyl)lithium

A mixture of 2-methoxypyridine (23.2 g) and diisopropylamine (1.35 mL) in THF (223 mL) was added to (trimethylsilylmethyl)lithium (218 mL, 13.8 weight percent in hexanes) at −20° C. The lithiation was 84% complete after 7 hours. Tri-isopropylborate (40.8 g) was added at −20° C. over 40 minutes. The mixture was stirred overnight at ambient temperature. 5 percent NaOH (aq, 225 mL) was added. The aqueous layer was removed and brought to pH 5 by adding 10% HCl (aq). The resulting white precipitate was isolated by filtration. After drying, 22.23 g of 2-methoxypyridine-3-boronic acid was obtained (68% yield).

Example 4

Deprotonation of Azaaromatic Using (trimethylsilylmethyl)lithium

A dry 50 mL 3-neck round bottom flask was charged with (trimethylsilylmethyllithium (20.9 mL, 12.7 weight percent) and cooled to −20° C. Tetrhydrofuran (15 mL) was added to the flask followed by the addition of 3-methoxypyridine (2.0 g). After 1 hour, chlorotrimethylsilane (2.6 mL) was added to the flask. The mixture was allowed to warm to ambient temperature overnight. The mixture was concentrated in vacuo and partitioned with 5 percent NaHCO₃ (10 mL) and methyl tert-butyl ether (15 mL). The methyl tert-butyl ether layers were combined, dried over MgSO₄ and concentrated, resulting in 2.61 grams of orange liquid. The product was purified by silica gel column chromatography to afford 1.76 grams of 3-methoxy-4-trimethylsilylpyridine (53% yield). The structure of the product was confirmed by gas chromatography and mass spectroscopy (molecular weight equal to 181) and $^1$H NMR (0.3 ppm, s, 9H); (3.9 ppm, s, 3H); (7.2 ppm, m, 1H); and (8.2 ppm, m, 2H).

Example 5

Stabilization of (trimethylsilylmethyl)lithium Using methyl tert-buty ether (MTBE)

A 3000 mL, Morton Cleve flask was oven-baked at 125° C. overnight. The flask was assembled hot with a dry ice condenser, mechanical stirrer, thermo-couple, and a Claisen adapter. The set up was allowed to cool under a purge of argon. Lithium metal powder (70.0 grams/10.1 moles) produced by FMC, Inc. was added to the flask along with 900 mL of hexane. The solution was then heated to reflux temperature, about 68.0° C. Once at reflux the heat source was reduced, chloromethyltrimethylsilane (531.41 grams/4.202 moles) was added drop wise. Reflux continued during the feed step of the process. At the end of the feed, the solution was allowed to stir at reflux for 0.5 hours. Once reflux had subsided, the solution was allowed to cool to approximately 20° C. A molar equivalent (1.0 equivalent/4.20 moles) of methyl tert-butly ether (MTBE) was added drop wise to the solution over a 15-minute period. An exotherm was noticed during the MTBE feed with a 12.8° C. increase in the temperature of the solution. Once the MTBE addition was complete, the solution was cooled gradually to about 25° C. and then filtered.

The resulting product included 1.50 grams of sample having 8.8 mL HCl and a normality of HCl 0.4946=27.45 percent. After storage at room temperature for a 7-day period, no pressure difference was noticed in the storage vessel the sample was free of any signs of decomposition. The sample was then subjected to a cold environment of 5° C. for several days. No formation of crystals occurred during the cold storage. The sample was further tested for pyrophoricity and found to be pyrophoric at 27.45 weight percent (trimethylsilylmethyl)lithium.

Example 6

Comparative Example

Attempted Stabilization of (trimethylsilylmethyl)lithium Using tetrahydrofuran (THF)

A 1000 mL, Morton Cleve flask was oven-baked at 125° C. overnight. The flask was assembled hot with a dry ice condenser, mechanical stirrer, thermo-couple, and a Claisen adapter. The set up was allowed to cool under a purge of argon. Lithium metal powder (8.0 grams/1.153 moles) produced by FMC, Inc. was added to the flask with 145 mL of hexane. The solution was heated to reflux temperature, about 68.0° C. Once at reflux, the heat source was reduced and chloromethyltrimethylsilane (68 grams/0.554 moles) was added drop wise to the flask. Reflux continued during the feed step of the process. At the end of the feed, the solution was allowed to stir at reflux for 1.5 hours. Once reflux had subsided, the solution was allowed to cool to approximately 20° C., after which a one molar equivalent (1.0 equivalent/1.153 moles) of tetrahydrofuran (THF) was added drop wise to the solution over a 15-minute period. An exotherm was noticed during the THF feed and a 25° C. increase in the temperature was noted. Once the THF addition was complete, the solution was cooled gradually to about 25° C. and then filtered.

The resulting product included a 1.93 gram sample having 7.8 mL HCl with a normality of HCl 0.4946=18.91 percent. The sample was stored at room temperature for 7 days. The sample produced a good deal of pressure and became slightly hazy with the formation of a white solid. Visible off gassing from the sample was noticed. A second total base calculation indicated 16.78 percent, which was a significant reduction from the first total base calculation. After one month, the sample solution changed to an almost red color and the sample included additional precipitant.

Example 7

Comparative Example

Formation of (trimethylsilylmethyl)lithium in MTBE

A 500 mL, Morton Cleve flask was oven-baked at 125° C. overnight. The flask was assembled hot with a dry ice condenser, mechanical stirrer, thermo-couple, and a Claisen adapter. The set up was allowed to cool under a purge of argon. Lithium metal powder (5.30 grams/0.764 moles) produced by FMC, Inc. was added to the flask along with 115 mL of MTBE. The solution was then heated to reflux temperature, about 56.0° C. Once at reflux, the heat source was reduced and chloromethyltrimethylsilane (44.97 grams/0.367 moles) was added drop wise to the flask. Reflux continued during the feed step of the process. During the feed step it was noticed that the MTBE was causing some problems with temperature control even with a hexane bath. At the end of the feed, the solution was still highly exothermic and reached a maximum temperature of 89.5° C. at one point during post reaction. The solution was cooled to room temperature and the sample was filtered. The filtration process was slow and included washing. The sample was clearly not soluble at 25 weight percent. The presence of white solids in the sample was noticed. Filter aide was employed during filtration. The sample became hazy and seemed viscous after storage overnight.

An attempt was made to obtain a total base calculation and the results indicated that the weight percent (trimethylsilylmethyl)lithium was less than 1.0 percent. Gas chromatography indicated that the sample was primarily 1,2-bis(trimethylsilyl)ethane.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A reaction mixture for deprotonating a pyridinic compound, comprising a pyridinic compound selected from the group consisting of pyridine, 4-methoxypyridine, 2-fluoropyridine, 2-methoxypyridine and 3-methoxypyridine, and a substituted alkylmetal reagent comprising a compound having the formula $R_3W—CH_2$-M, wherein R is selected from the group consisting of alkyl groups, aryl groups, and Si; W is selected from the group consisting of carbon, Si, and Sn; and M is at least one metal selected from the group consisting of lithium, sodium, potassium, cesium, manganese, zinc, and magnesium.

2. The reaction mixture of claim 1, wherein the substituted alkylmetal reagent is a silyl alkylmetal reagent.

3. The reaction mixture of claim 2, wherein the silyl alkylmetal reagent is selected from the group consisting of (trimethylsilylmethyl)lithium and neopentyllithium.

4. The reaction mixture of claim 1, wherein M is lithium.

5. The reaction mixture of claim 1, further comprising tetrahydrofuran.

6. The reaction mixture of claim 1, further comprising $HCONR_2$, wherein R is an alkyl.

7. The reaction mixture of claim 1, wherein the pyridinic compound is 4-methoxypyridine and the substituted alkyl-metal reagent is (trimethylsilylmethyl)lithium.

* * * * *